United States Patent [19]

Hata

[11] 4,403,341
[45] Sep. 6, 1983

[54] EMERGENCY INFORMATION COMMUNICATING DEVICE

[76] Inventor: Kiyoshi Hata, 4-16, Uenodori 4-chome, Nada-ku, Kobe-shi, Hyogo-ken, Japan

[21] Appl. No.: 352,584

[22] Filed: Feb. 26, 1982

[30] Foreign Application Priority Data

Feb. 26, 1981 [JP] Japan .................................. 56/27123
Apr. 1, 1981 [JP] Japan .................................. 56/49699

[51] Int. Cl.³ .......................................... H04B 1/034
[52] U.S. Cl. .................................. 455/100; 455/128; 340/539
[58] Field of Search ...................... 455/91, 95, 97, 100, 455/128, 129; 340/539

[56] References Cited

U.S. PATENT DOCUMENTS

| | | | |
|---|---|---|---|
| 1,993,436 | 3/1935 | Eberhard | 455/100 |
| 3,335,239 | 8/1967 | Fey | 455/128 |
| 3,846,704 | 11/1974 | Bessette | 455/100 |
| 4,335,375 | 6/1982 | Schaeffer | 455/128 |

FOREIGN PATENT DOCUMENTS 2725449 12/1978 Fed. Rep. of Germany ...... 455/100

Primary Examiner—Jin F. Ng
Attorney, Agent, or Firm—Birch, Stewart, Kolasch & Birch

[57] ABSTRACT

Emergency information communicating device is disclosed having a wireless transmission circuit, a switch means and a battery which are provided in a waterproof case body, a permanent magnet inserted in a slot defined in the case body for providing a magnetic field to actuate the switch means and an electrical conducting member acting as an antenna. By disengaging the permanent magnet from the case body, emergency information can be radiated from the antenna.

7 Claims, 9 Drawing Figures

EMERGENCY INFORMATION COMMUNICATING DEVICE

FIELD OF THE INVENTION

The present invention relates to an information communicating device utilizing a wireless transmitter, and in particular, it relates to an emergency information communicating device using a transmitter assembled in the form of such as a necklace and a pendant so as to be always put on the user's body to ensure an easy operation.

BACKGROUND OF THE INVENTION

It is well known that in case of a fit of an acute geriatric disorder such as cerebral apoplexy and a heart attack, prompt medical treatment is required. Particularly in the case an old person or an invalid person living by himself who has such an attack, he must immediately send information to the emergency hospital or to another person by himself.

In general, a telephone can be utilized as a means for sending information when such an attack occurs. However, it may be difficult to reach the telephone in a sudden fit, and even if the person reaches the telephone, it might be impossible to handle the telephone itself.

As an emergency information communicating device utilizing the telephone, the Japanese Telegraph and Telephone Corporation (Nihon Denshin Denwa Kosha) has provided an automatic emergency information communicating device for old persons living alone, which is called "ANSHIN" and is driven by the simple operation of a push button to automatically call a previously-selected partner. However, such a device requires operation of the push button at the location of the device or by an attached extension cord, and transmission of the emergency information cannot be conducted unless the user of the device restricts his activity within the scope of the length thereof.

There has further been provided an alarm system against fires and invaders, which is called "Domestic Safety System—My Alarm" by Nihon Keibi Hosho Kabushiki Kaisha—Secom 24 Kabushiki Kaisha. This alarm system receives an electromagnetic wave transmitted from a respectively independent automatic or manual electromagnetic wave transmitter in case of a fire or an emergency situation by a fixed receiver provided in the user's house called "Home Controller" and automatically sends information to an information control room of the guarding company by an automatic telephone call device called "Dialler" which is connected with the fixed receiver. The manually-operated transmitter of the system called "Emergency Button" may also serve as a device for sending information on the occurrence of the aforementioned fit of the old person, though, it is large and heavy, and not waterproof. Further, it is not suited for always putting on the user's body and is held in an exclusive holder hung on the wall, and in the emergency case, the emergency push button switch on the transmitter must be pushed by breaking a guard plate provided thereon for preventing erroneous operation as in the case of a fire alarm. Thus, it is difficult to certainly operate the device by hand in the case of the attack of the sudden illness. Further, the device might slip off when the user falls down, and thus may not afford an opportunity to use the device.

The aforementioned conventional emergency information communicating devices are complicated in construction employing a large number of components, leading to malfunction and a high price.

SUMMARY OF THE INVENTION

Accordingly, an essential object of the present invention is to provide an emergency information communicating device which can be easily operated for starting communication.

Another object of the present invention is to provide an emergency information communicating device which is small and light so that the device can be easily put on a human body.

A still further object of the present invention is to provide a waterproof emergency information communicating device to assure emergency information communication even if the device is dropped in the water such as in a bath.

Yet, still a further object of the present invention is to provide an emergency information communicating device cheap in cost and having a long life.

Still a further object of the present invention is to provide an emergency information communicating device having a display means for displaying an emergency message when emergency signals are generated so as to assure transferring of the emergency message to others such as neighbors or a passersby.

According to the present invention, there is provided an emergency information communicating device which comprises a case body enclosing in a waterproof manner a high-frequency transmission circuit, a battery for supplying a DC power source to the transmission circuit, a switch means operable by a magnetic field, the switch means being connected between the battery and the transmission circuit, a slot defined in the case body close to the switch means, being separated by a partition wall member; a permanent magnet which can be inserted into the slot to apply a magnetic field for operating the switch means and an elongated electric conducting member, one end of which is connected with the end portion of the permanent magnet and the other end connected with the output terminal of the transmission circuit, the switch means being turned off when the permanent magnet is inserted in the predetermined position in the slot and being turned on when the permanent magnet is displaced from the predetermined position, thereby starting the transmission circuit which radiates electromagnetic waves from the electric conducting member.

The device, according to the present invention, can be put on the user's body in the form of, for example, a transmission pendant and a necklace serving as a transmission antenna, and in case of an attack of sudden illness, the device can be simply, roughly and easily operated by pulling the transmission pendant and disengaging the same from the necklace to start transmission of an emergency electromagnetic wave, which is received by a fixed receiver previously set in the user's house for sending information in case of an emergency.

BRIEF EXPLANATION OF THE DRAWINGS

FIG. 3b is an enlarged view showing a modification of a part shown in FIG. 3a;

DESCRIPTION OF THE PREFERRED EMBODIMENTS

Figure 1:
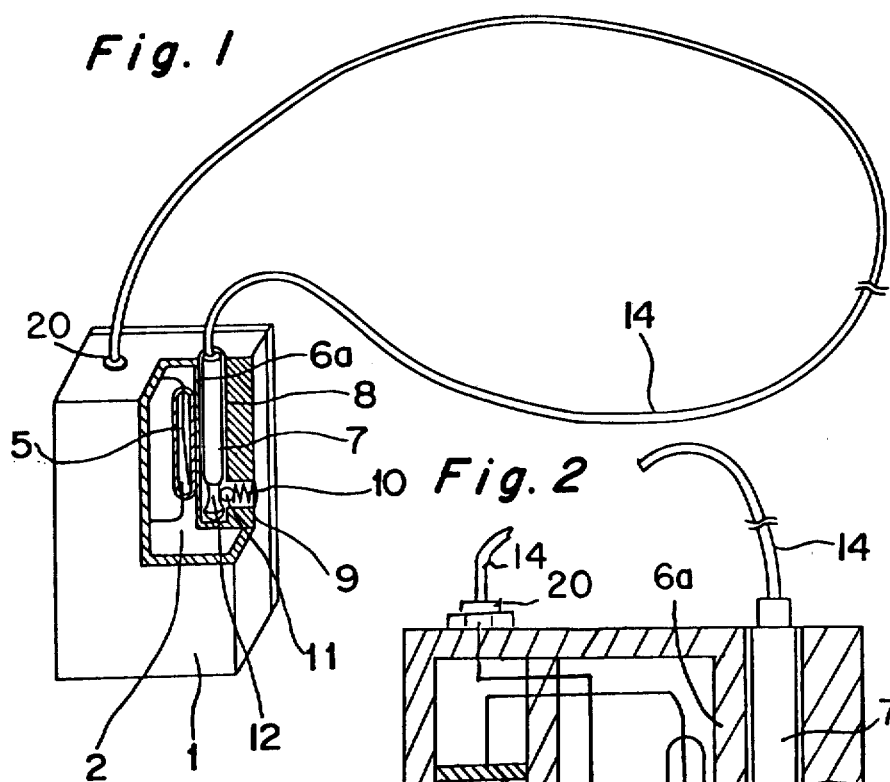
FIG. 1 is a partial fragmentary perspective view of the wireless information communicating device according to the present invention.
Figure 2:
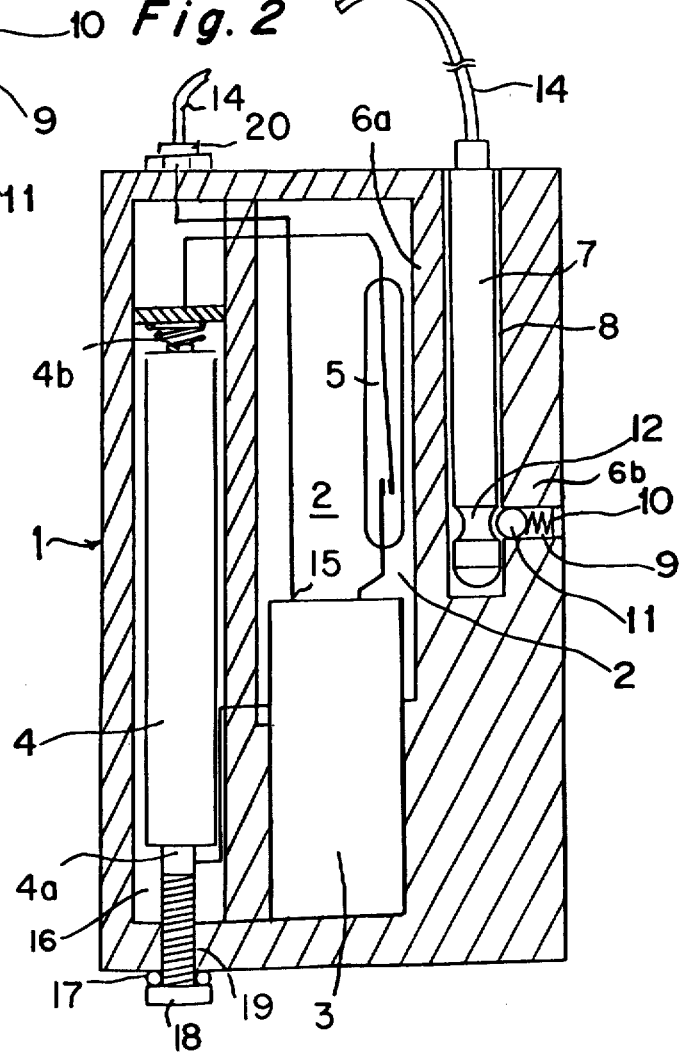
FIG. 2 is an enlarged cross sectional view of the device of FIG. 1.

Referring now to FIGS. 1 and 2, there is shown a case body 1 formed by a plastic resin in the form of a generally rectangular-shaped pendant having a square-shaped space 2 therein containing a wireless transmitter 3, a lithium battery 4 for supplying DC power to the transmitter 3 and a reed switch 5 for starting the transmitter 3. The case body 1 is formed by a molding technique to provide the closed waterproof space 2.

The reed switch 5 is fixed in parallel with and close to a partition wall 6a dividing the space 2. An elongated slot 8 for receiving a column-shaped permanent magnet 7 is defined in the case body 1 in the outside of the space 2. This slot 8 extends from the top of the case body 1 to the vicinity of the bottom end of the reed switch 5 in parallel with the wall 6a. The permanent magnet 7 can be inserted into the slot 8, and when the permanent magnet is in a predetermined position as shown in FIG. 1, the reed switch 5 is switched "off" by the magnetic field of the same. On the other hand, when the permanent magnet 7 is disengaged from the slot 8, the reed switch 5 is turned on.

Since the case body 1 is formed in a water-proof manner by molding, the space 2 keeps out water allowing for conducting certain transmitting operation even when the case body 1 is in water.

In a portion near the bottom of the slot 8, a recess 9 is formed horizontally in the side wall 6b of the case body 1 for containing a spring 10 with a ball 11, and a part of the spherical surface of the ball 11 slightly projecting into the slot 8. In the lower end portion of the permanent magnet 7, there is formed a groove 12 which is semicircular in cross section for snappingly engaging with the ball 11.

Figure 3A:
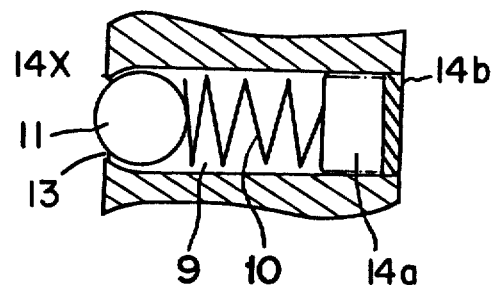
FIG. 3a is an enlarged view showing a part of FIG. 2.

As shown in FIG. 3a in detail, the ball 11 is prevented from excessively projecting into the slot 8 by an engaging member 14x having a small opening 13 which is smaller in diameter than the recess 9. The spring 10 is pushed by a screw 14a. The outer face of the screw 14a may be closed by resin material 14b.

By virtue of the aforementioned construction, when the permanent magnet 7 is inserted completely into the slot 8 as shown in FIG. 2, the ball 11 is elastically engaged with the groove 12 formed in the lower end portion of the permanent magnet 7 to prevent the permanent magnet 7 from disengaging from the slot 8.

Figure 3B:
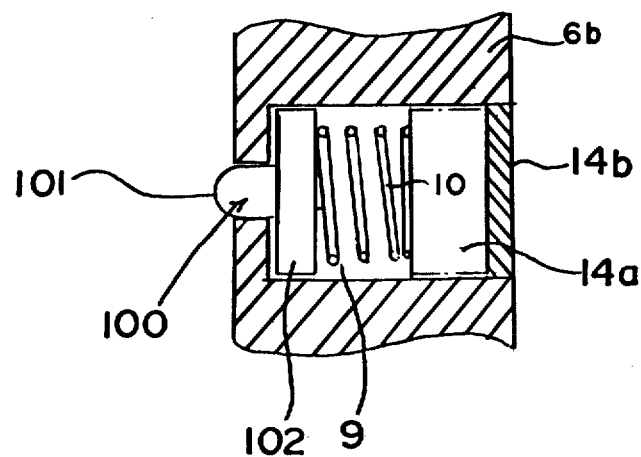

For snap engagement of the permanent magnet 7 in the slot 8, another embodiment is shown in FIG. 3b in which, in place of the ball 11, a small columnar member 100 having a spherical end 101 and a flanged end plate 102 can be used.

An end of a wire 14 made of electrically conductive material serving both as a necklace for hanging on a human neck and an antenna is connected with one end of the permanent magnet 7, and the other end of the wire 14 is electrically and mechanically connected to an antenna terminal 15 of the transmitter 3 through a suitable connector 20 secured on the top of the case body 1.

The battery 4 is contained in a hole 16 formed in the case body 1, and an opening 19 of the hole 16 is sealed in a watertight manner by a screw 18 engaged with an O-ring 17. By using the lithium battery as a power source, the device can be used for a long period such as about 5 years.

One electrode 4a of the battery 4 is connected with one terminal for the power source for the transmitter 3 while the other electrode 4b is connected with the other terminal for the power source of the transmitter 3 through the reed switch 5.

Figure 4:
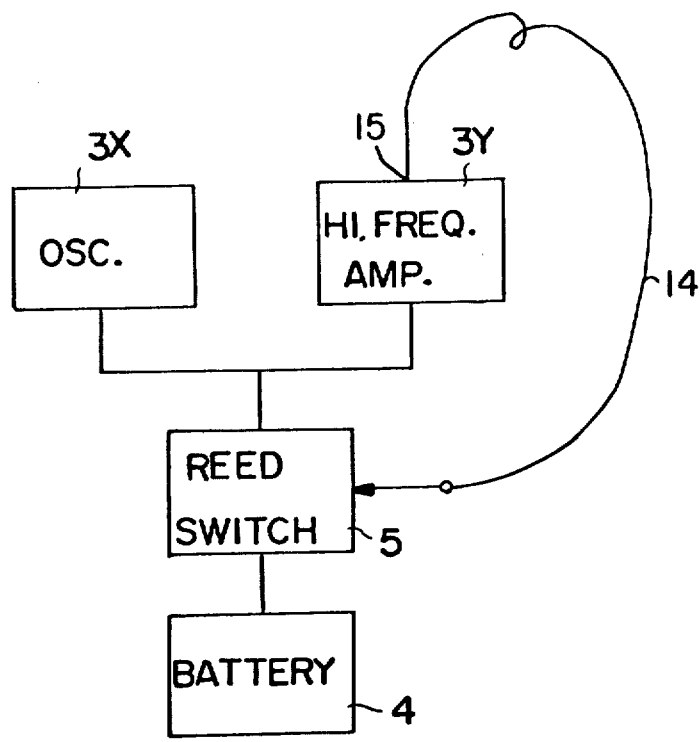
FIG. 4 is a circuit diagram employed in the device shown in FIG. 1.

FIG. 4 shows an electrical circuit of the aforementioned wireless information communicating device according to the present invention, in which the battery 4 is connected to the power supply terminals of a high-frequency oscillator 3X and a high-frequency amplifier 3Y of the wireless transmitter 3, and the antenna terminal of the high-frequency amplifier 3Y is connected with the wire 14.

Figure 5:
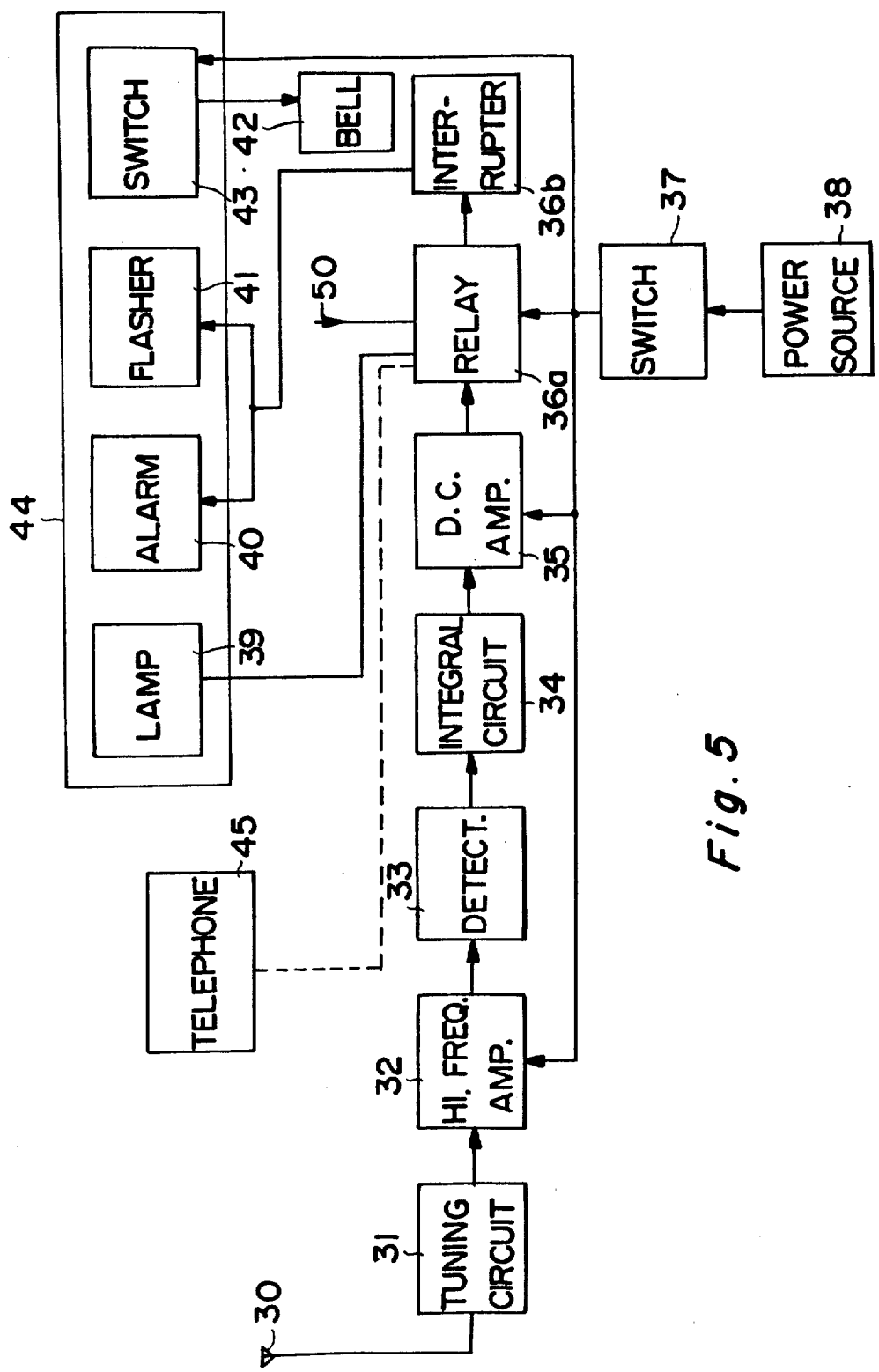
FIG. 5 is a circuit diagram of a fixed receiver which is associated with the wireless information communicating device shown in FIG. 1.

FIG. 5 is a circuit diagram showing a fixed receiver for receiving electromagnetic waves transmitted from the transmitter 3 of FIGS. 1 and 2 which comprises a receiving antenna 30, a tuning circuit 31, a high-frequency amplifier 32, a detector 33, an integral circuit 34, a DC amplifier 35, a relay circuit 36a, an interrupter 36b, a power supply switch 37 and a power source 38. The fixed receiver further includes an alarm system 44 integrally formed by a display lamp 39 for asking sending of emergency information to others, an intermittent alarm 40, a red-light flasher 41, an electric confirmation bell 42 for confirming whether the alarm is real or in error and a confirmation bell switch 43. The arrow 50 indicates a reset button of the relay circuit 36a. The fixed receiver is installed in the house of the user of the aforementioned wireless information communicating device.

Figure 6:
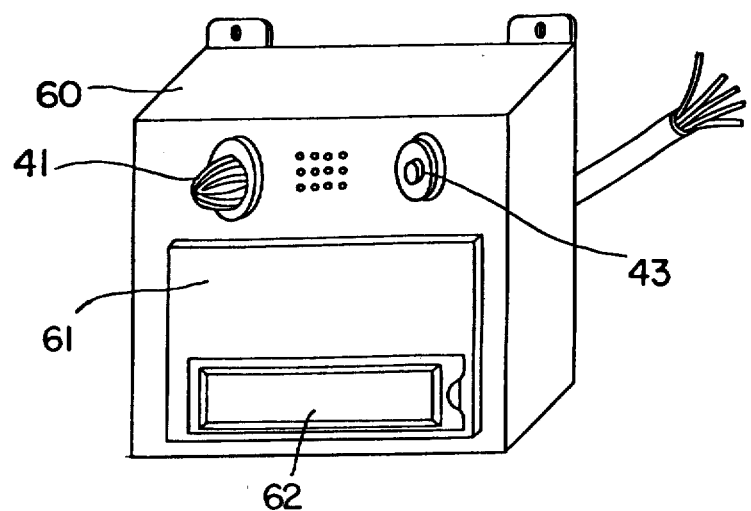
FIG. 6 is a perspective view of an alarm system of the fixed receiver.

FIG. 6 shows a body 60 of the alarm system 44, and the display panel 61 is made of, e.g., an opaline plastic plate with red letters displayed thereon giving a message such as "The owner of this device has come down by illness. Please push the bell button and confirm whether the alarm is in error or not. If no reply is received, please call an emergency hospital since he has been suddenly attacked by illness." Such an indication comes out by lighting up of the display lamp 39 contained inside the body 60 of the alarm system 44, and a paper sheet 62 indicating the address, name and telephone number of the user is located under the display. The intermittent alarm 40, the red-light flasher 41 and the confirmation bell switch 43 are provided on the panel surface of the body 60 of the alarm system 44.

OPERATION

When the permanent magnet 7 is inserted into the slot 8 and the ball 11 is engaged with the groove 12, the reed switch 5 is turned off and the transmitter 3 is not operated. In this condition, the wire 14 is put around the user's neck to suspend the case body 1 on the user's breast as a pendant. On the other hand, the power supply switch 37 of the fixed receiver as shown in FIG. 5 is turned on so that the emergency information communicating device according to the present invention is ready to operate. In this condition, the device is capable of sending information on emergency at any time and any place within the area of receiving of the electromagnetic wave from the transmission case body 1. The area of communication between the transmitter 3 and the fixed receiver is set with the radius of about 50 m in this embodiment. In the case of an attack, e.g., a sudden illness, the transmission case body 1 suspended on the user's breast is downwardly pulled by hand so that the permanent magnet 7 is disengaged from the slot 8. By virtue of this, the reed switch 5 is turned on and a power source is applied from the battery 4 to the transmitter 3 so as to start the transmitting operation. Then the high-frequency oscillator 3X and the high-frequency amplifier 3Y are operated so as to transmit a predetermined electromagnetic wave from the antenna formed by the wire 14 which is connected with the high-frequency amplifier 3Y. In the meantime, the fixed receiver as shown in FIG. 5 is ready to operate, and the electromagnetic wave transmitted from the antenna 14 is received by the receiving antenna 30 thereby fed to the tuning circuit 31 and the received signal is amplified by the high-frequency amplifier 32, then, detected by the detector 33 to generate a DC voltage. The DC voltage is inputted into the integral circuit 34, and if the electromagnetic wave transmitted from the antenna 14 does not last over a predetermined period defined by a time constant of the integral circuit 34, the output voltage of the integral circuit 34 cannot reach a predetermined level. On the other hand, when the electromagnetic wave is continued longer than the predetermined period, and when the output voltage of the integral circuit 34 rises over the predetermined level after the predetermined period, this output signal is inputted to the DC amplifier 35. The predetermined period is set for 20 seconds in this embodiment. The predetermined period is set for preventing the device from erroneous operation by obstacle electromagnetic waves radiated from electric appliances, thunderbolts or automobiles and for securing certain operation of the relay circuit 36a connected to the output of the DC amplifier 35. When the DC amplifier 35 is turned on, the relay circuit 36a is operated to turn the display lamp 39 on by supply of electricity through the make contact of the relay circuit 36a, and simultaneously the interrupter 36b starts operation and the relay circuit 36a is self-held so as to thereafter continue its operation regardless of reception of the electromagnetic wave. The alarm system 44 is set in advance of usage of the device in a conspicuous position such as in front of the gate of the user's house. Simultaneously, the interrupter 36b intermittently supplies electric power to the intermittent alarm 40 and to the red-light flasher 41 so that the intermittent alarming sound and flashing of the red light with call attention of neighbors or passerbys to report to them that the user is in an emergency by the indication on the display panel 61 on which the message is illuminated by the display lamp 39. The alarming operation continues until the power supply switch 37 of the fixed receiver shown in FIG. 5 is opened or the reset button 50 of the fixed receiver is pushed to release self-holding of the relay circuit 36a.

Numeral 45 indicates an automatic telephone emergency information communicating device utilizing the telephone circuit, which is, if necessary, connected to another make contact of the relay circuit 36a to transfer the signal transmitted from the wire 14 to the automatic telephone emergency information communicating device.

If the user always bears it in mind to pull the transmission situation in an emergency case, it may be possible to close the reed switch 5 by pulling the transmission case body 1 even in the worst case that the user loses his senses after the attack. For example, since the paralysis in case of a fit of cerebral apoplexy always takes place on the left or right half of the body and not on the whole body, the transmission case body 1 of the device according to the present invention can be simply and easily pulled to disengage the permanent magnet 7 from the case body 1 by one hand even if the body of the user is enfeebled by physical collapse.

Figure 7:
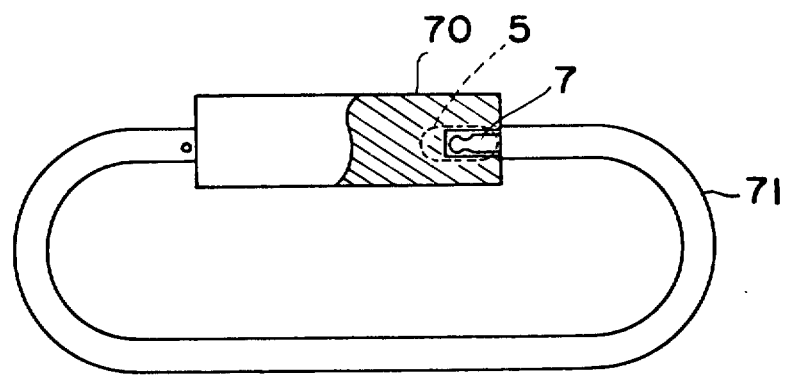
FIG. 7 is a side view of another embodiment of an emergency information communicating device according to the present invention.
Figure 8:
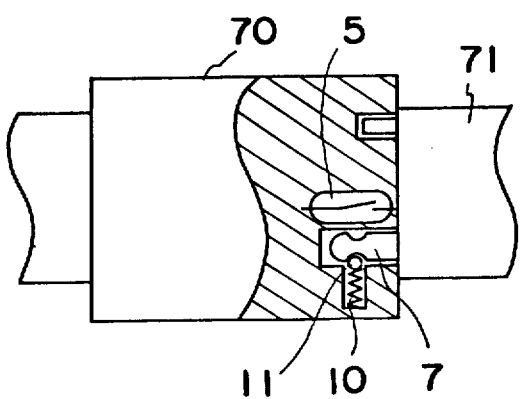
FIG. 8 is a part of plan view of FIG. 7.

FIGS. 7 and 8 show another embodiment of the present invention, in which the high-frequency transmitter (not shown) and the reed switch 5 and the battery (not shown) are installed in a case body 70 formed as a wrist watch. In this embodiment, one end of a flexible band 71 is provided with the permanent magnet 7 formed in a similar manner as shown in FIG. 1.

Normally, the one end of the band 71 is engaged with the case body 70 by insertion of the permanent magnet 7 into the slot and the other end of the band 71 is fixed to the case body 70 and is connected to the output terminal of the high-frequency transmitter.

When the permanent magnet 7 is inserted in a position as shown in FIGS. 7 and 8, the reed switch 5 is opened and the transmitter is stopped.

On the other hand, when the permanent magnet 7 is disengaged from the case body 70 by pulling the band 71, the reed switch 5 is on and the transmitter can be operated to start radiating electromagnetic waves from the band 71.

According to the present invention, since the case body is formed waterproof, when the case body 1 or 70 is dropped in water, which may occur when the user is in a bath, the transmitting device can operate to radiate electromagnetic wave, thereby assuring communication of the emergency information.

Although the present invention is explained with reference to the preferred embodiments herein, various modification can be made. For example, the case body 1 or 70 can be made of a non-magnetic metallic material. Also, the reed switch can be replaced by other types of switch means operable by a magnetic field.

What is claimed is:
1. An emergency information communicating device which comprises:
  a waterproof case body enclosing a high-frequency transmission circuit, a battery for supplying a DC power source to the transmission circuit, and switch means operable by a magnetic field, said switch means being connected between the battery and the transmission circuit;
  a slot defined in the case body close to the switch means, said slot and switch means being separated by a partition wall member;
  a permanent magnet for inserting into a predetermined position of said slot to apply a magnetic field for operating the switch means; and
  an elongated electric conducting member, one end of which is connected with an end portion of said permanent magnet and the other end connected with an output terminal of said transmission circuit, said switch means being turned off when said permanent magnet is inserted in the predetermined position in said slot and being turned on when the permanent magnet is displaced from the predetermined position, thereby starting the transmission circuit to radiate an electromagnetic wave from said electric conducting member.

2. An emergency information communicating device according to claim 1, wherein said switch means is a reed switch.

3. An emergency information communicating device according to claim 2, wherein said device further comprises means for snappingly securing said permanent magnet in the said predetermined position in said slot.

4. An emergency information communicating device according to claim 3, wherein said securing means comprises an engaging member movably projected into said slot to elastically engage a recessed portion formed in said permanent magnet to retain said permanent magnet in said predetermined position.

5. An emergency information communicating device according to claim 1, wherein said case body has a generally cubic configuration in said form of a pendant and said electrical conducting member is a wire acting as a necklace.

6. An emergency information communicating device according to claim 1, wherein said case body is in the form of a wrist watch and said electrical conducting member is a band connected with said case body.

7. An emergency information communicating device which comprises:

a waterproof case body enclosing a high-frequency transmission circuit, a battery for supplying a DC power source to the transmission circuit, and switch means operable by a magnetic field, said switch means being connected between the battery and the transmission circuit;

a slot defined in the case body close to the switch means, said slot and switch means being separated by a partition wall member;

a permanent magnet for inserting into a predetermined position of said slot to apply a magnetic field for operating the switch means; and an elongated electric conducting member, one end of which is connected with an end portion of said permanent magnet and the other end connected with an output terminal of said transmission circuit, said switch means being turned off when said permanent magnet is inserted in the predetermined position in said slot and being turned on when the permanent magnet is displaced from the predetermined position, thereby starting the transmission circuit to radiate an electromagnetic wave from said electric conducting member, said device further comprising a fixed receiver for receiving the electromagnetic wave radiated from the electrical conducting member and display means for displaying a message in response to an output signal of the receiver.

* * * * *